United States Patent
Anderson et al.

(10) Patent No.: US 11,717,317 B2
(45) Date of Patent: Aug. 8, 2023

(54) METHOD AND APPARATUS FOR TISSUE HARVESTING

(71) Applicant: THE GENERAL HOSPITAL CORPORATION, Boston, MA (US)

(72) Inventors: Richard R. Anderson, Boston, MA (US); Walfre Franco, Worcester, MA (US); Joel N. Jimenez-Lozano, Cambridge, MA (US); William A. Farinelli, Danvers, MA (US)

(73) Assignee: The General Hospital Corporation, Boston, MA (US)

( * ) Notice: Subject to any disclaimer, the term of this patent is extended or adjusted under 35 U.S.C. 154(b) by 285 days.

(21) Appl. No.: 14/421,592

(22) PCT Filed: Aug. 14, 2013

(86) PCT No.: PCT/US2013/054955
§ 371 (c)(1),
(2) Date: Feb. 13, 2015

(87) PCT Pub. No.: WO2014/028626
PCT Pub. Date: Feb. 20, 2014

(65) Prior Publication Data
US 2015/0216545 A1    Aug. 6, 2015

Related U.S. Application Data

(60) Provisional application No. 61/682,969, filed on Aug. 14, 2012.

(51) Int. Cl.
*A61B 17/322*    (2006.01)
*A61B 10/02*     (2006.01)
(Continued)

(52) U.S. Cl.
CPC ........ *A61B 17/322* (2013.01); *A61B 10/0233* (2013.01); *A61M 1/79* (2021.05);
(Continued)

(58) Field of Classification Search
CPC . A61B 10/02; A61B 10/0233; A61B 10/0266; A61B 10/0275; A61B 10/0283;
(Continued)

(56) References Cited

U.S. PATENT DOCUMENTS 4,930,997 A * 6/1990 Bennett ............... A61M 1/0019
  417/410.1
6,027,512 A   2/2000 Bridges
(Continued)

FOREIGN PATENT DOCUMENTS

WO    9829149 A1    7/1998
WO   2009/146068 A1   12/2009
(Continued)

OTHER PUBLICATIONS

Wikipedia; Subcutaneous tissue; https://en.wikipedia.org/wiki/Subcutaneous_tissue; accessed Oct. 18, 2017.*
(Continued)

*Primary Examiner* — Diane D Yabut
*Assistant Examiner* — Rachel S Highland
(74) *Attorney, Agent, or Firm* — Quarles and Brady

(57) ABSTRACT

Exemplary methods and devices can be provided for harvesting a plurality of small tissue pieces, e.g., having widths less than about 1 mm or 0.5 mm, using one or more hollow needles. A fluid can be flowed through a conduit past the proximal ends of the needles to facilitate removal of the tissue pieces from the needle lumens, and can maintain the tissue pieces in a controlled and protective liquid environment. A filter can be used to extract and collect the tissue pieces from the liquid, or the tissue pieces can be deposited
(Continued)

directly onto a porous dressing. Such tissue pieces can be used as microscopic grafts, which can be applied directly to a wound site or provided on a substrate or dressing, or stored for later use. Such microscopic grafts can promote tissue regrowth and wound healing, or can be applied to a scaffold to grow new tissue.

16 Claims, 6 Drawing Sheets

(51) Int. Cl.
    *A61M 1/00*         (2006.01)
    *A61B 17/3205*    (2006.01)
    *A61B 17/00*       (2006.01)
    *A61B 17/30*       (2006.01)

(52) U.S. Cl.
    CPC ..... *A61B 10/0283* (2013.01); *A61B 17/32053* (2013.01); *A61B 2017/00752* (2013.01); *A61B 2017/306* (2013.01); *A61B 2017/3225* (2013.01); *A61B 2217/005* (2013.01)

(58) Field of Classification Search
    CPC ............ A61B 2010/045; A61B 17/322; A61B 17/32053; A61B 2017/3225; A61B 2017/00969; A61B 2017/00752; A61B 2010/0225; A61B 2017/306; A61B 2217/005; A61M 1/0056; A61M 1/0001–0098
    USPC .................. 600/562, 564, 565, 566, 567
    See application file for complete search history.

(56) References Cited

U.S. PATENT DOCUMENTS

| | | | |
|---|---|---|---|
| 6,440,086 | B1 | 8/2002 | Hohenberg |
| 6,537,242 | B1* | 3/2003 | Palmer ............ A61M 37/0015 600/309 |
| 7,651,507 | B2 | 1/2010 | Mishra et al. |
| 7,926,401 | B2 | 4/2011 | Mishra et al. |
| 8,226,664 | B2 | 7/2012 | Drews et al. |
| 8,696,686 | B2 | 4/2014 | Drews et al. |
| 9,017,343 | B2 | 4/2015 | Westerling, Jr. et al. |
| 9,060,803 | B2 | 6/2015 | Anderson et al. |
| 9,084,465 | B2 | 7/2015 | Oostman, Jr. et al. |
| 9,119,945 | B2 | 9/2015 | Simons et al. |
| 2004/0186421 | A1* | 9/2004 | Freeman ............ A61B 10/0035 604/39 |
| 2005/0137525 | A1* | 6/2005 | Wang ................ A61M 37/0015 604/93.01 |
| 2005/0143713 | A1 | 6/2005 | Delmore et al. |
| 2005/0274679 | A1 | 12/2005 | Kao |
| 2007/0156164 | A1* | 7/2007 | Cole ................ A61B 17/32053 606/187 |
| 2007/0179401 | A1* | 8/2007 | Hibner ............... A61B 10/0275 600/568 |
| 2008/0208146 | A1 | 8/2008 | Brandwein et al. |
| 2008/0234602 | A1* | 9/2008 | Oostman ........... A61B 10/0266 600/564 |
| 2008/0249553 | A1* | 10/2008 | Gruber ............ A61B 17/32002 606/171 |
| 2010/0191253 | A1 | 7/2010 | Oostman, Jr. et al. |
| 2011/0313429 | A1* | 12/2011 | Anderson .......... A61B 10/0233 606/131 |
| 2012/0010527 | A1* | 1/2012 | Sundheimer ....... A61B 10/0233 600/566 |
| 2012/0041430 | A1* | 2/2012 | Anderson ........ A61B 17/32053 606/13 |
| 2012/0271320 | A1 | 10/2012 | Hall et al. |
| 2012/0289985 | A1* | 11/2012 | Motai ................ A61B 10/0233 606/185 |
| 2014/0200484 | A1 | 7/2014 | Austen et al. |
| 2015/0238214 | A1 | 8/2015 | Anderson et al. |
| 2015/0258319 | A1 | 9/2015 | Simmers |
| 2015/0320990 | A1 | 11/2015 | Burton et al. |
| 2016/0082241 | A1 | 3/2016 | Burton et al. |
| 2016/0121091 | A1 | 5/2016 | Burton et al. |
| 2016/0136406 | A1 | 5/2016 | Berry et al. |

FOREIGN PATENT DOCUMENTS

| | | |
|---|---|---|
| WO | 2011/140497 A2 | 11/2011 |
| WO | WO-2012103488 A1 | 8/2012 |
| WO | WO-2012103492 A1 | 8/2012 |

OTHER PUBLICATIONS

Dua et al.; Follicular Unit Extraction Hair Transplant; 2010; J Cutan Aesthet Surg. May-Aug. 2010; 3(2):76-81. (Year: 2010).*
International Search Report under dated Dec. 19, 2013 in connection with PCT/US2013/054955.
Extended European Search Report issued by the European Patent Office for European Patent Application No. 13829700.7 dated May 20, 2016 (7 pgs.).
European Patent Office Extended European Search Report for application 19182350.9, dated Sep. 12, 2019.
European Patent Office, Communication, Application No. 19182350.9, dated Aug. 27, 2020, 4 pages.
European Patent Office, Extended Search Report, Application No. 22150983.9, dated Apr. 7, 2022, 8 pages.

* cited by examiner

METHOD AND APPARATUS FOR TISSUE HARVESTING

CROSS-REFERENCE TO RELATED APPLICATION(S)

This application represents the national stage entry of PCT International Application No. PCT/US2013/054955 filed Aug. 14, 2013, which claims the benefit of U.S. Provisional Patent Application Ser. No. 61/682,969, filed Aug. 14, 2012, both of which are incorporated herein by reference for all purposes.

STATEMENT REGARDING FEDERALLY SPONSORED RESEARCH

This invention was made with government support under W911NF-10-1-0017, W911NF-12-1-0086, and W911NF-11-1-0122 awarded by the Army Research Laboratory—Army Research Office. The government has certain rights in the invention.

TECHNICAL FIELD

The present disclosure relates to method and apparatus for fluid-assisted harvesting of small tissue specimens from a donor site.

BACKGROUND INFORMATION

Various approaches to tissue copying and grafting are being developed, in which small columns of tissue (microscopic tissue columns, or MTCs) are removed from a donor site and can be used in various procedures such as e.g., being introduced into a recipient site, implanted in a matrix, etc. Such approaches are described, e.g., in International Patent Publication No. WO 2009/146068.

The MTCs are typically less than about 1 mm in diameter and their removal is well-tolerated by the donor site. For example, the holes formed in a donor site by removal of MTCs can heal rapidly with little or no visible scar or marking formed because of the small size of the holes and their being surrounded by healthy tissue. These columns of living tissue can nucleate and/or stimulate growth of new tissue. The small size of the MTCs favors their survival in various environments.

The MTCs can be harvested using a hollow needle. However, they tend to be fragile tissue samples that can be adversely affected by their surroundings and handling, e.g., they may be contaminated or mechanically stressed after being cut or otherwise separated and then removed from the donor site. Accordingly, it is desirable to provide a method and apparatus for harvesting MTCs that facilitates their rapid extraction from a donor site and subsequent retrieval and storage without damaging them.

Accordingly, there may be a need to address and/or overcome at least some of the issues indicated herein above.

SUMMARY OF EXEMPLARY EMBODIMENTS

According to exemplary embodiments of the present disclosure, method and apparatus can be provided for harvesting small samples of biological tissue (e.g. microscopic tissue columns, or MTCs that are typically less than about 1 mm in width, and, may be longer in length. The removal of such small MTCs can be well-tolerated by the donor site. For example, the small regions of damage in the donor site caused by removal of the tissue samples (e.g., MTCs) heal rapidly with little or no formation of visible scars.

In certain exemplary embodiments of the present disclosure, the method and apparatus can facilitate harvesting MTCs that uses one or more hollow needles to extract the MTCs from a tissue donor site. For example, an apparatus can be provided that includes one or more hollow harvesting or 'coring' needles, preferably extending from a housing. The distal end of the needle is configured to penetrate the tissue, so that a portion of tissue (an MTC) will be cut away from the surrounding tissue by the needle tip and walls, and located in a distal portion of the hollow lumen of the needle. The MTC can be removed from the surrounding tissue and remain in the lumen of the needle when the needle is withdrawn. An inner diameter of the hollow needle can be less than about 1 mm in diameter, e.g., between about 0.15 mm and 0.5 mm, for cosmetic treatments involving skin. In further exemplary embodiments, larger diameters may be used to harvest samples from other tissues or organs that may be more tolerant of damage and/or for which visible scarring is not problematic.

A conduit can be provided in the apparatus that is configured to circulate a fluid past a proximal end of each coring needle. The lumen of the hollow needle can be in fluid communication with the conduit. The flowing fluid helps to draw the MTC up through the lumen of the needle and into the fluid path after the MTC is separated from surrounding tissue, where the MTC can then be surrounded by a protective fluid environment.

A filter arrangement that can include, e.g., a filter element, a mesh basket, or the like, can be provided in the flow path of the circulating fluid such that the harvested MTCs within the flowing fluid can then be trapped in the filter arrangement while the fluid passes through. In certain exemplary embodiments of the present disclosure, the filter arrangement can be provided in a chamber, and a cap or cover can be provided to facilitate access to the harvested MTCs. A vent can optionally be provided to release air that may be entrained in the fluid during harvesting of the MTCs.

According to further exemplary embodiments of the present disclosure, the fluid containing, entrained MTCs can be directed by a delivery arrangement onto a porous dressing or substrate external to the site. For example, MTCs can be deposited directly from the flowing liquid onto a porous dressing, and the dressing with MTCs can then be applied directly to a wound site. The delivery arrangement and substrate can be moved relative to one another such that. MTCs are deposited over a particular region of the dressing/substrate during the harvesting procedure. In still further exemplary embodiments of the present disclosure, the porous dressing can be provided as pant of the filter arrangement.

The fluid characteristics can be selected to provide a gentle environment for the MTCs, to prevent contamination, and/or to promote their viability and growth. The fluid can be temperature-controlled using conventional thermal control systems. The fluid can contain a variety of substances, including saline, growth factors, buffers, etc. Various sensors and controllers can optionally be provided, e.g., to monitor and/or control such parameters as fluid temperature and flow rate, fluid composition, pressure at various locations within the apparatus, etc.

An actuator such as a solenoid, a motor with a rotary/linear converter, or the like can be provided to direct the needles into the donor tissue and then withdraw them. Such actuators can be controlled using a conventional power source and controller arrangement.

According to additional exemplary embodiments of the present disclosure, a lower portion of the exemplary apparatus can be shaped to create a recess between the tissue surface and a lower surface of the apparatus. One or more ducts can be provided in communication with this enclosed space, and a source of low pressure can be connected to the ducts to pull the tissue surface upward, thereby stretching and stabilizing the tissue to facilitate penetration by the needles. An elevated pressure can optionally be connected to the ducts after penetration by the needles to push the tissue back down. In certain embodiments, the needles can be held stationary with respect to the lower surface of the apparatus, and an alternating low and high pressure can be applied to pull the tissue onto the needles and then pull it away from them.

These and other objects, features and advantages of the present disclosure will become apparent upon reading the following detailed description of exemplary embodiments of the present disclosure, when taken in conjunction with the appended drawings and appended claims.

BRIEF DESCRIPTION OF THE DRAWINGS

Further objects, features and advantages of the disclosure will become apparent from the following detailed description taken in conjunction with the accompanying figures showing illustrative embodiments, results and/or features of the exemplary embodiments of the present disclosure, in which.

Figure 1A:
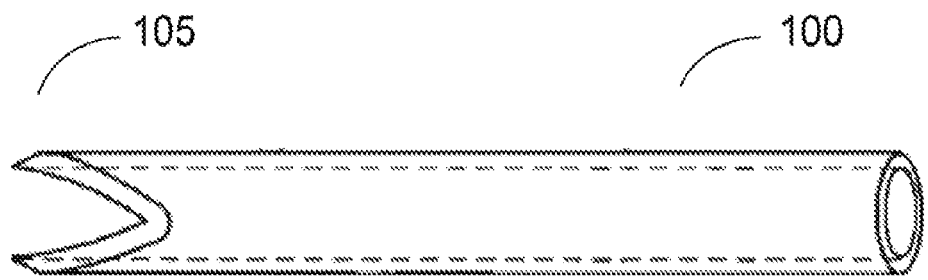
FIG. 1A is an illustration of an exemplary harvesting needle that can be used with exemplary embodiments of the present disclosure.

Throughout the drawings, the same reference numerals and characters, unless otherwise stated, are used to denote like features, elements, components, or portions of the illustrated embodiments. Similar features may thus be described by the same reference numerals, which indicate to the skilled reader that exchanges of features between different embodiments can be done unless otherwise explicitly stated. Moreover, while the present disclosure will now be described in detail with reference to the figures, it is done so in connection with the illustrative embodiments and is not limited by the particular embodiments illustrated in the figures. It is intended that changes and modifications can be made to the described embodiments without departing from the true scope and spirit of the present disclosure as defined by the appended claims.

DETAILED DESCRIPTION OF THE PREFERRED EMBODIMENTS

The present disclosure relates to a method and apparatus for harvesting microscopic tissue columns (MTCs) that uses one or more hollow needles to extract the MTCs from a tissue donor site. An apparatus can be provided that: includes one or more hollow harvesting or 'coring' needles.

An illustration of a side perspective view of an exemplary hollow harvesting needle 100 is provided in FIG. 1A. The inner diameter of the needle 100 can be selected to approximately correspond to a particular diameter of a tissue sample or MTC to be removed from the donor site as described herein. For example, 18, 19 or 20 gauge biopsy needles (e.g., having an inner diameter of 0.838 mm, 0.686 mm and 0.564 mm, respectively) or the like can be used to form the tube. In general, needles having a gauge size between 18 and 30 or the equivalent can be used for cosmetic applications such as skin resurfacing. In general, the inner diameter of such needle 100 (e.g., the diameter of the central lumen) can be, e.g., between about 1 mm and about 0.15 mm, or preferably between about 0.5 mm and about 0.15 mm. Such smaller inner diameters can be used to separate and remove MTCs having a similar width from surrounding tissue. MTCs having such small widths may exhibit desirable viability, for example, because nutrients can more readily be transported directly to more cells in the MTC from surrounding environment. A hollow needle or tube 100 having a slightly larger or smaller inner diameter can also be used in further embodiments, e.g. based on the type of tissue being harvested, if larger or smaller MTCs are desired. For example, larger diameters may be used to harvest samples from tissues or organs other than skin that may be more tolerant of damage and/or for which visible scarring is not problematic.

Figure 1B:
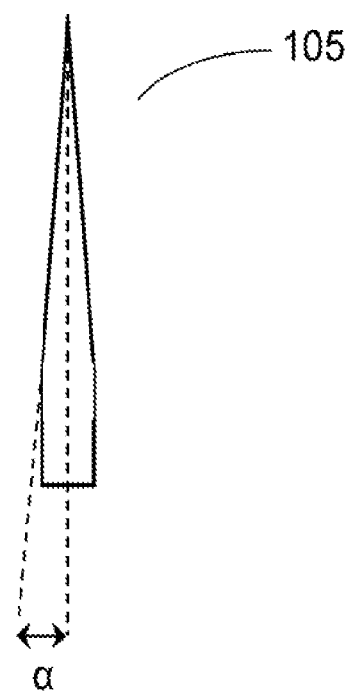
FIG. 1B is an illustration of the tip region of an exemplary harvesting needle.

The harvesting needle 100 shown in FIG. 1A includes a distal end that can be formed as a plurality of piercing arrangements (e.g., including points) 105. A side view of a distal end of the needle 100 is shown in FIG. 1B. For example, the two exemplary points 105 shown in FIG. 1A can be formed by grinding flat bevels on opposite sides of the needle 100 at an angle α relative to the long axis of the needle, as shown in FIG. 1B. The angle α can be, e.g., between about 10° and about 25°, or between about 10° and 20°. Such narrow tip angles can facilitate penetration of the needle 100 into tissue and a severing of tissue within the lumen of the needle 100 from adjacent tissue as the needle 100 is advanced. In further exemplary embodiments, the distal end of the harvesting needle 100 can be provided with three or more points 105, e.g., by forming three or more angled flat bevels at different orientations, and optionally at different angles.

The exemplary points 105 and associated beveled edges can facilitate insertion of the distal end of the needle 100 into donor-site tissue and removal of MTCs therefrom. For example, the distal end of the harvesting needle 100 can be configured to penetrate the tissue, so that a portion of tissue (an MTC) will be cut away from the surrounding tissue by the needle tips 105 and adjacent beveled edges, such that the MTC will be located in the hollow lumen of the needle 100. The needle 100 can be formed of metal or another structurally rigid material, e.g., hypodermic stainless steel tubing or the like. For example, the needles 100 can be formed from a small biopsy needle or a similar structure. A portion of the needle 100 can optionally be coated with a lubricant or low-friction material, such as Teflon®, to further facilitate passage of the needle 100 through the donor site tissue. In certain exemplary embodiments of the present disclosure, a rotating motion can be applied around the longitudinal axis of the needle 100 during insertion to facilitate penetration of the needle 100 into the tissue and/or separation and removal of an MTC from the surrounding tissue.

Exemplary harvesting needles 100 were formed by grinding angled bevels into opposite sides of a surgical steel hypodermic needle to form two points, as illustrated schematically in FIGS. 1A and 1B. The bevel angle $\alpha$ was about 12°. Thin wall hypodermic needles of 19 and 22 gauge, and regular-wall needles of 25 and 30 gauge were used. These exemplary needles 100 were inserted into samples of pig and human skin tissue to a depth of the subcutaneous fat layer, and the penetration force was measured. The width of the resulting harvested MTCs was also measured. Data for this study is summarized in Table 1 below.

TABLE 1

Mean diameter, D, of harvested MSTC and harvesting penetration force, F, for needles of different gauges: regular wall (RW), thin wall (TW), outer diameter (od), inner diameter (id). Mean force was obtained from two users and four independent measurements per user. Mean diameter was obtained from five independent measurements. Standard deviation of the mean is in parenthesis.

| Harvesting-Needle | | MSTC | F [N] | |
| --- | --- | --- | --- | --- |
| Gauge | od [μm] | id [μm] | D [μm] | pig | human |
| 19TW | 1070 | 810 | 820 (97) | 13.6 (2.29) | 6.5 (1.99) |
| 22TW | 710 | 510 | 520 (45) | 8.45 (1.58) | 4.8 (1.15) |
| 25RW | 510 | 250 | 380 (84) | 8.24 (0.778) | 4.8 (0.86) |
| 30RW | 311 | 159 | NA | 4.3 (0.385) | NA |

In general, the width of a harvested MTC was observed to correspond closely with the inner (lumen) diameter of the harvesting needle 100. Insertion force of any needle into human tissue was about 50-60% of the force needed to insert the same needle into pig skin tissue. For typical needle sizes that may be used to harvest skin tissue in humans, the force measured to insert a single needle 100 was about 5-6 N. If a plurality of needles 100 are inserted simultaneously, the total force required would, to a first approximation, be about 5 N multiplied by the number of needles 100 being inserted. Such force data can be used, e.g., to estimate the force requirements for devices having a plurality of harvesting needles 100, and can also set limits on how many such needles 100 can be inserted using a reasonable degree of force.

Figure 2:
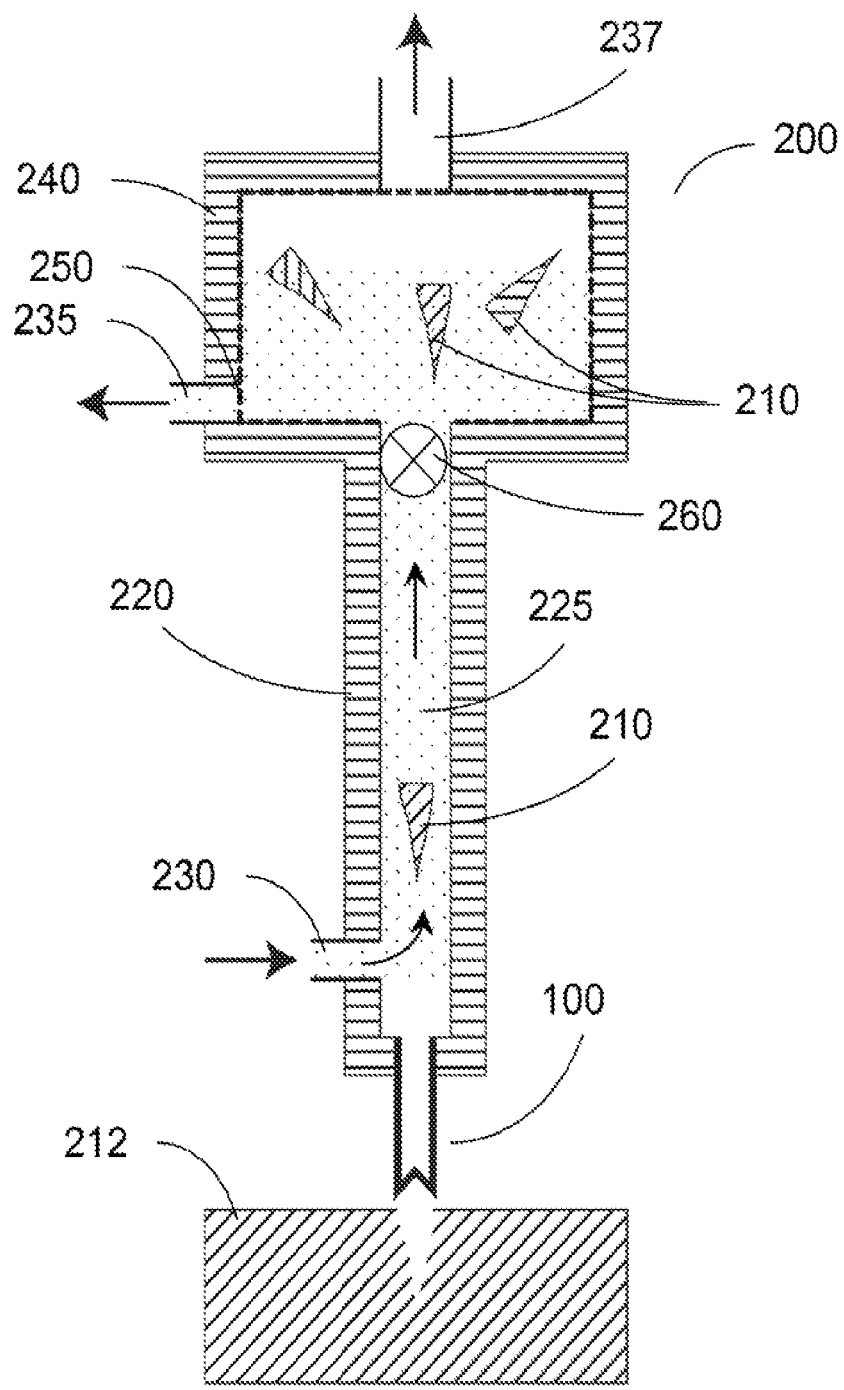
FIG. 2 is a cross-sectional view of a diagram of an exemplary apparatus for harvesting tissue samples in accordance with exemplary embodiments of the present disclosure.

A cross-sectional view of a diagram of an apparatus 200 in accordance with certain exemplary embodiments of the present disclosure is shown in FIG. 2. The exemplary apparatus 200 shown in FIG. 2 can include a housing 220 with a fluid conduit 225 provided therein. One or more harvesting needles 100 can be coupled to the housing 220. The fluid conduit 225 can be provided, with at least one fluid inlet 230 and at least one fluid outlet 235. The fluid conduit 225 can be configured or structured such that a fluid can flow therethrough; e.g., the direction of fluid flow is indicated by the arrows in FIG. 2. A proximal end of the needle lumen can be in a fluid communication with the conduit 225. For example, the fluid can flow past a proximal end of the harvesting needle 100, as shown in FIG. 2.

In one exemplary procedure to harvest MTCs 210 from a donor tissue 212, as illustrated in FIG. 2, the exemplary apparatus 200 can be manipulated such that the distal end of one or more of the harvesting needles 100 penetrate the tissue 212 to a particular depth. The depth can be selected and/or controlled, e.g., by providing or adjusting a particular distance between the bottom of the housing 220 and the distal end of the one or more needles 100. For example, a penetration depth can be selected that extends the distal end of one or more of the harvesting needles 100 through the entire local thickness of the dermis to about the depth of the subcutaneous fat layer, or optionally slightly into this fat layer. Inserting the needles 100 through the entire thickness of the dermis can provide an MTC 210 that has the full length of the dermis. Further, such exemplary depth can facilitate a separation of the MTC 210 from the surrounding tissue, because the proximal end of the needle 100 can cut the MTC 210 away from the adjacent dermal tissue, and the MTC 210 can then be fully detached by tearing a small amount of subcutaneous fat at the bottom of the MTC 210. Such fatty tissue may be more easily separable than denser dermal tissue. After the needle 100 is withdrawn from the donor site tissue 212, an MTC that was separated from the surrounding tissue 212 can remain within the lumen of the needle 100.

The fluid flowing through the conduit 225 can reduce pressure at the proximal end of the needle 100, which can facilitate removal of the MTC 210 from the lumen of the needle 100. The MTC 210 can be entrained in the flowing liquid, and carried through the conduit 225 and into a chamber 240. The flowing fluid can be withdrawn from the fluid outlet 235, which can be provided as part of the chamber 240. MTCs that have been harvested as described herein can remain in the chamber 240. One or more optional vents 237 can be provided in an upper portion of the chamber 240 (or conduit 225, if no chamber is provided) to allow any air entrained during the harvesting procedure to escape from the conduit pathway, e.g., to prevent the chamber 240 from filling with air. For example, a small amount of air may be sucked in through the needle 100 along with an MTC 210 when the needle 100 is withdrawn from the donor tissue 212.

In some exemplary embodiments of the present disclosure, the conduit 225 can form a closed loop for the fluid flow or otherwise recirculate fluid flowing through the apparatus 200. For example, the fluid inlet 230 and outlet 235 shown in FIG. 2 can be connected to the outlet and inlet, respectively, of a fluid pump arrangement (not shown) or the like.

The pump arrangement can be or include an external pump or similar device configured to circulate fluid through the conduit 225. The fluid can be provided from one or more reservoirs, and the pump arrangement and the conduit 225 can be configured, connected or structured such that the fluid leaving the chamber 240 via the outlet 235 can be discarded. In further exemplary embodiments of the present disclosure, the fluid exiting the outlet 235 can be recirculated through the conduit 225, e.g., in a closed-loop configuration. One or more sensors (e.g. pressure or flow rate sensors—not shown) can optionally be provided in the apparatus to facilitate control of the circulating fluid. In certain exemplary embodiments of the present disclosure, the pump arrangement can be or include a peristaltic pump. The flowing fluid can facilitate the removal of the MTCs 210 through the hollow needle 100 and into the fluid path, where the MTCs 210 are surrounded by it gentle fluid environment.

A "trap" or filter arrangement 250 can be provided in the apparatus to remove harvested MTCs 210 from the circulating fluid and hold them for subsequent transfer or further processing. For example, an optional filter arrangement 250 can be provided in the chamber 240, e.g., near the outlet 235, to retain harvested MTCs within the chamber during the exemplary tissue harvesting procedure, as shown in FIG. 2.

The filter arrangement 250 can include, e.g., a chamber or an enlarged region provided in the fluid circulation path of the conduit 225. The filter arrangement 250 can also include a permeable filter element, e.g. a mesh, woven or porous material, basket, trap, or the like such that the circulating fluid flows at least partially through the chamber 240 and the filter element.

A pore size or permeability of the filter arrangement 250 can be selected to facilitate the fluid flow therethrough while preventing the MTCs 210 from doing so. For example, the pore size can be less than about 200 microns, e.g., about 100 microns or less. Such exemplary pore sizes can facilitate the flow of the circulating fluid through the filter arrangement 250 with a relatively little restriction, while being small enough to trap and retain the MTCs 210 that can be suspended in the flowing fluid. Accordingly, the harvested MTCs 210 can be retained in the trap while the fluid can flow therethrough, and exit from the filter arrangement 250, e.g., through the outlet 235.

According to certain exemplary embodiments of the present disclosure, the filter arrangement 250 can include a porous dressing with holes or pores sufficiently small to trap MTCs 210 while facilitating or allowing the fluid to flow through it. The dressing can be 'populated' with MTCs after the exemplary harvesting procedure, and it can be removed from the apparatus and applied directly onto a wound site. Such dressing as the filter element can be used with any of the various embodiments described herein.

In certain exemplary embodiments of the present disclosure, a source of low pressure (not shown) can optionally be provided in communication with the conduit 225, e.g., to reduce pressure in the fluid conduit 225 and further facilitate fluid flow and/or removal of MTCs 210 from the harvesting needle 100. For example, the chamber 240 can be configured or structured to provide a headspace for a gas, such as air, above the filter arrangement 250. The source of low pressure can include, e.g., a vacuum pump, a low-pressure line or the like. The low-pressure source can be in fluid communication with this headspace, e.g., via a tube or hose connected to an opening in the chamber 240, such as the vent 237 shown in FIG. 2. Other similar or equivalent exemplary configurations can also be provided to generate a reduced pressure in the conduit 225 according to further exemplary embodiments of the present disclosure.

According to further exemplary embodiments of the present disclosure, the exemplary apparatus 200 can include one or more control arrangements (not shown). For example, a pressure sensor can be provided at one or more locations within the apparatus 200 to detect, e.g., the pressure within the fluid conduit 225 near the harvesting needle 100 or a pressure differential across the filter arrangement 250 to ascertain if the filter arrangement 250 is clogged and may be impeding, fluid flow. Such exemplary sensors can be provided in communication with, e.g., a fluid pump arrangement and/or an optional low-pressure source as described herein, to control or adjust the operation of such components and maintain preferred conditions for the apparatus 200 during the exemplary operation. Other exemplary sensors that can be provided and can include, for example, temperature sensors to monitor and optionally control the fluid temperature, an optical sensor adjacent to or within the conduit 225 to detect a presence of MTCs 210 flowing therethough, and/or one or more sensors configured to monitor characteristics of the fluid flowing through the apparatus 200. In further embodiments, a location sensor can be provided on or next to the needle 100 or within the apparatus 200 to detect a position of the needle 100 relative to the bottom surface of the housing 220, e.g., to track or monitor the penetration depth of the needle 100 during use. Such exemplary sensors and control arrangements, and/or a low-pressure source, can be used with any of the various embodiments described herein, including those embodiments illustrated in FIGS. 3 and 4.

In still further exemplary embodiments of the present disclosure, a cauterizing arrangement can be provided on one or more needles 100. For example, RF current can be provided to one or more of the harvesting needles 100 in the apparatus 200. The cauterizing arrangement can be used to reduce or prevent bleeding during or after the harvesting procedure. For example, RF current can be applied to one or more of the needles 100 after the MTCs 210 have been withdrawn from the needle lumens, and before the needles 100 are fully withdrawn from the tissue 212 to avoid damaging the MTCs 210 while cauterizing the area around the removed volume of tissue.

According to yet further exemplary embodiments of the present disclosure, one or more control valves (not shown) can optionally be provided at one or more locations in the conduit 225. For example, a valve 260 can be provided between the proximal end of the coring needle 100 and the chamber 240 and/or filter arrangement 250, as shown in FIG. 2. The valve 260 can be kept open during harvesting of tissue columns 210, to allow and/or facilitate fluid containing such MTCs 210 to flow therethrough. The valve 260 can be periodically and/or momentarily closed while fluid is circulating, e.g., while the needle 100 is not located within the tissue of the donor site 212, which can direct some fluid entering the inlet 230 through the coring needle 100 and out of the distal end thereof, which can clean and/or unblock the lumen of the needle 100.

The fluid can be selected to provide a gentle environment for the MTCs 210, e.g., to prevent mechanical damage or contamination, and/or to promote their viability and growth. The fluid can be temperature-controlled using conventional thermal control systems. For example, the fluid can be provided from a source reservoir or container, and the temperature and/or other conditions of the fluid reservoir can be controlled using conventional control systems. The fluid can contain a variety of substances including, for example, saline, growth factors, buffers, etc. For example, the fluid can contain supplemental nutrients such as, e.g., amino acids, glucose, electrolytes, and/or oxygen to promote or help maintain viability of the harvested MTCs 210. The fluid can also include or comprise a conventional tissue culture medium, such as Dulbecco's Modified Eagle Medium, F12, or the like. Antibiotics (e.g., penicillin, streptomycin, or the like) and/or antifungal agents (e.g., amphotericin or fluconazole) can optionally be provided in the fluid to help disinfect the MTCs 210 after they are removed from the donor site 212.

In the various exemplary embodiments described herein, the MTCs 210 can be maintained in a controlled fluid environment from the time they are pulled up from the harvesting needle(s) 100 and flow through the conduit 225 until they are captured or deposited on the filter arrangement 250, which can also be maintained within the fluid. Accordingly, the MTCs 210 are less likely to be damaged or contaminated as compared to, e.g., other tissue removal devices that may expose removed tissue samples to air and/or other non-sterile surfaces.

Figure 3A:
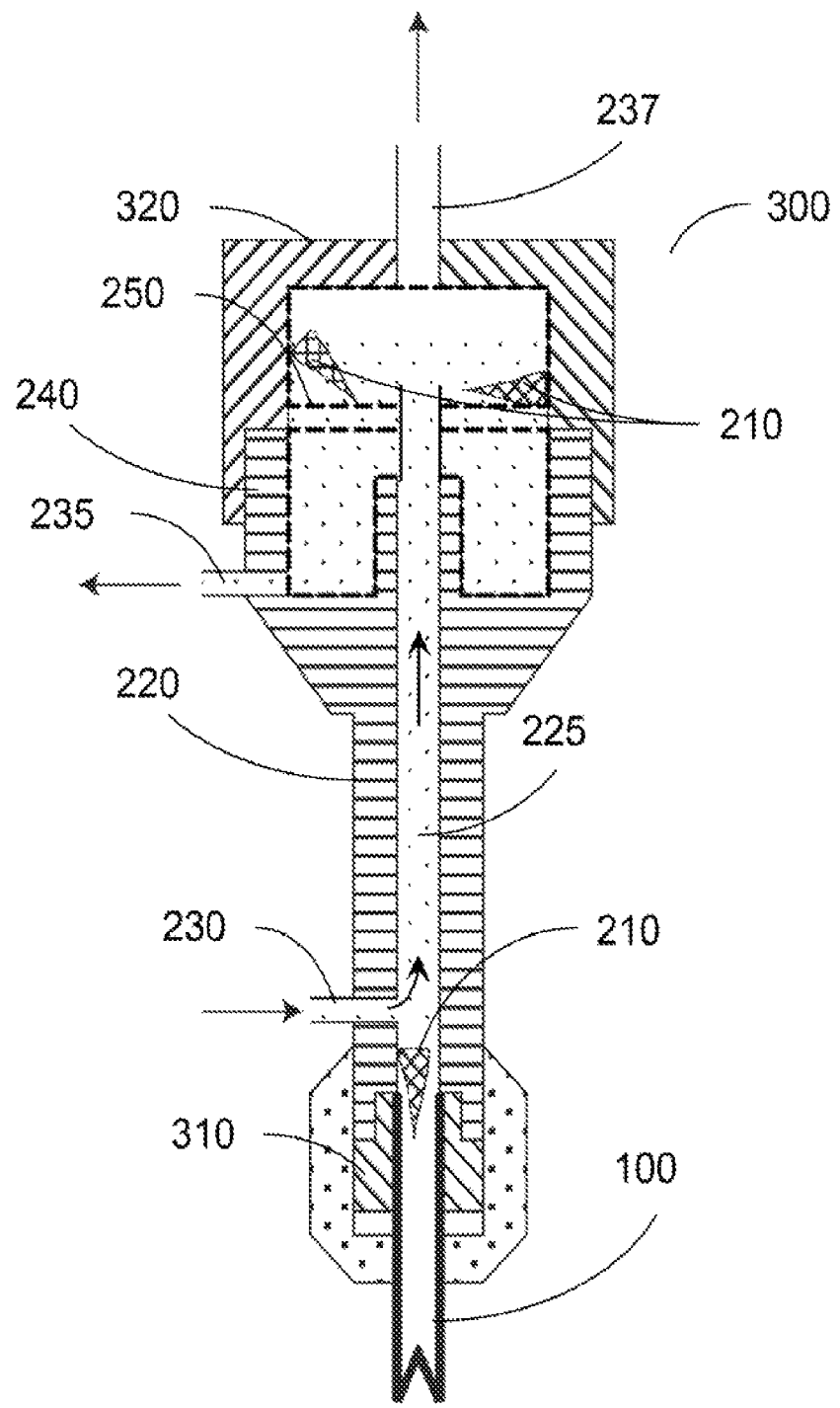
FIG. 3A is a cross-sectional view of a diagram of the exemplary apparatus for harvesting tissue samples in accordance with further exemplary embodiments of the present disclosure, in one exemplary operation.

FIG. 3A shows a cross-sectional view of a diagram of an apparatus 300 in accordance with further exemplary embodiments of the present disclosure. The apparatus 300 shown in FIG. 3A can be operated manually, and it has many features similar to those shown and described for the apparatus 200 in FIG. 2, e.g., but not limited to, the housing 220 with the fluid conduit 225, the harvesting needle(s) 100, the fluid inlet 230, the outlet 235, the upper chamber 240, the optional vent 237, and the filter arrangement 250. Certain differences between the exemplary embodiments of the apparatus 200 illustrated in FIG. 2 and the apparatus shown in FIG. 3A are described herein.

For example, one or more of the harvesting needles 100 can be attached or affixed to a hub 310. The hub 310 can be provided, e.g., as a shaped disc or in another geometry with one or more harvesting needles 100 affixed to it. The hub 310 can be configured such that it can fit into a shaped recess in the housing 220, to facilitate removal and replacement of the harvesting needle(s) 100 during or between harvesting procedures. A protrusion distance of the harvesting needle(s) 100 beyond the bottom surface of the apparatus 300, which can correspond to a penetration depth of the needle(s) 100 into tissue, can be adjusted using an adjusting arrangement such as, a threaded screw coupler provided in the housing, or the like. In certain embodiments, one or more needles 100 can be provided with a hub 310, where a desired penetration depth of the needles 100 into the tissue of the donor site can be determined or selected based on a predetermined distance between the hub 310 and the distal end of the needle(s) 100. A hub 310 such as that shown in FIG. 3A, which can include one or more of the needles 100, can be used with any of the various exemplary embodiments described herein.

The chamber 240 can be provided with a removable cap 320, or the like, to facilitate access to the interior of the chamber and removal of MTCs 210 that may be trapped or retained by the filter arrangement 250. For example, the exemplary apparatus 300 can include the filter arrangement 250 provided in the chamber 240, where the filter arrangement 250 can be located between an end of the conduit 225 and the fluid outlet 235. Such configuration facilitates the flow of fluid containing the harvested MTCs 210 through the filter arrangement 250 and out of the outlet 235, where the MTCs 210 can be retained by the filter arrangement 250. Access to the MTCs 210 after they are harvested and trapped can be achieved, e.g., by removing the cap 320 from the chamber 240.

According to additional exemplary embodiments of the present disclosure, the filter arrangement 250 and optionally the cap 320 can be provided, for example, as a sterile cartridge that can be inserted into the chamber 240 before harvesting MTCs 210, and can later be removed with the harvested MTCs 210. In still further exemplary embodiments of the present disclosure, the filter arrangement 250 can be provided as a removable "basket" or the like that can be inserted into the chamber 240, and removed with trapped MTCs 210 after the harvesting procedure is completed.

In an exemplary operation, similar to the exemplary operation of the exemplary apparatus 200 described herein, the exemplary apparatus 300 can be pressed onto a donor tissue site, such that the distal end of the harvesting needle 100 pierces the tissue and separates an MTC 210 from the surrounding tissue. The fluid flowing through the conduit 225 can facilitate withdrawal of the MTC 210 from the proximal end of the harvesting needle 100 such that it flows with the fluid through the conduit 225. The flowing fluid can transport the MTC 210 to the filter arrangement 250, where the MTC 210 can be retained by a mesh or other filter element, while the fluid flows through the filter arrangement 250 and exits the outlet 235, where it can optionally be recirculated. The apparatus 300 can be withdrawn from the donor site, and inserted into another location to harvest a further MTC 210. This process can be repeated a plurality of times to harvest a number of MTCs 210 from the donor site. After a sufficient number of MTCs 210 have been harvested, the filter arrangement 250 (or a portion thereof) containing the MTCs 210 can be removed from the apparatus 300 for further handling or processing.

Figure 3B:
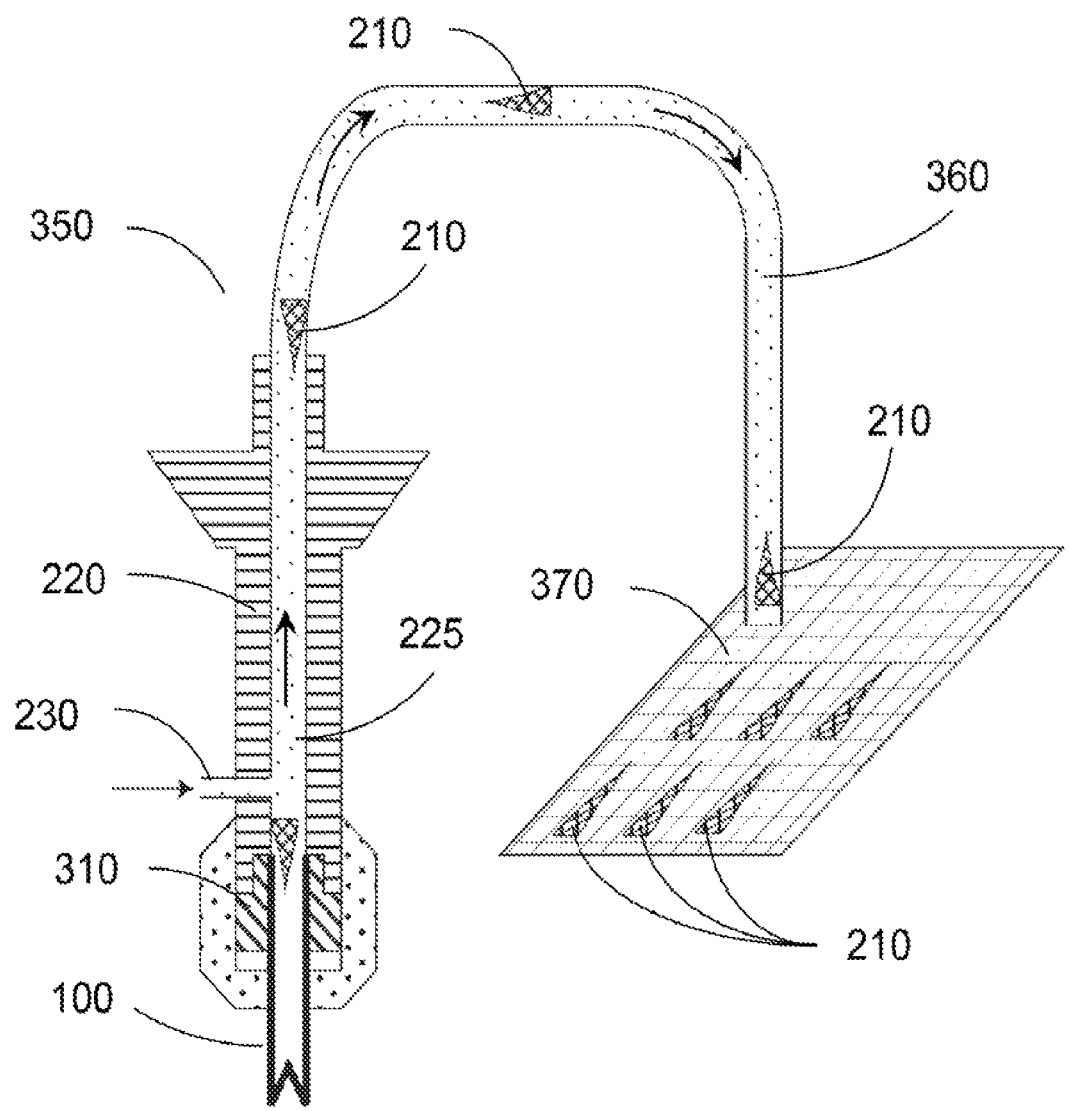
FIG. 3B is a cross-sectional view of a diagram of the exemplary apparatus for harvesting tissue samples in accordance with yet further exemplary embodiments of the present disclosure in another exemplary operation.

Another exemplary apparatus 350 is shown in FIG. 3B that can include several features in common with the other exemplary apparatuses 200, 300, e.g., the housing 220 with the fluid conduit 225, the harvesting needle(s) 100, and the fluid inlet 230. The exemplary apparatus 350 illustrated in FIG. 3B can be provided with a delivery arrangement 360 configured to direct at least a portion of the fluid flowing from the inlet 230 and through the conduit 225 onto a receiving substrate 370 (which can be or act as a filter arrangement). The delivery arrangement 360 can include rigid and/or flexible tubing, or the like, which can be connected to the conduit 225.

The receiving substrate 370 can be or include, e.g., a filter element that can trap MTCs 210 while allowing fluid from the conduit 225 to flow through or off of the substrate 370. In further exemplary embodiments of the present disclosure, the substrate 370 can be or include a permeable or porous dressing material, which can act as a filter element to trap MTCs 210 thereon while allowing the fluid to pass through or flow off of the substrate 370. In this exemplary manner, harvested MTCs 210 can be directly deposited, onto a dressing or the like, and such dressing with the MTCs 210 can then be transported or applied directly to a wound site.

The distal end of the delivery arrangement 360 can be positionable such that it traverses a predetermined region of the substrate 370 during the harvesting procedure, e.g., while fluid containing MTCs 210 flows through the conduit 225 and out of the distal end of the delivery arrangement 360. For example, at least a portion of the delivery arrangement 360 can be flexible, such that the distal end thereof can be positioned and/or moved over the substrate 370 while the housing 220 containing the needle(s) 100 can be advanced and withdrawn over multiple locations of the donor site to harvest MTCs 210.

In a further exemplary embodiment of the present disclosure, the distal end of the delivery arrangement 360 can be held or maintained in a stationary position, and the substrate 370 can be controllably moved or translated relative to this distal end such that MTCs 210 are deposited over a predetermined area of the substrate 370.

The translation of the distal end of the delivery arrangement 360 relative to the substrate 370 (or vice versa) can be performed, using any one of various translation arrangements known in the art. Such positional translators can include, e.g., one or more motors or actuators, various arms, supports, clamps, pivots, or the like, along with any sensors and/or controllers that may be used to control a rate and/or direction of motion, limits of motion or displacement, etc. For example, the relative motion of the distal end of the delivery arrangement 360 and the substrate 370 can be selected and/or performed such that MTCs 210 are deposited in a predetermined spacing, pattern or density on the substrate 370. The deposition geometry can be estimated in a straightforward manner based on the frequency at which the needle 100 is inserted into tissue to obtain a new MTC 210, together with the speed and direction of the relative motion between the distal end of the delivery arrangement 360 and the substrate 370.

Figure 4A:
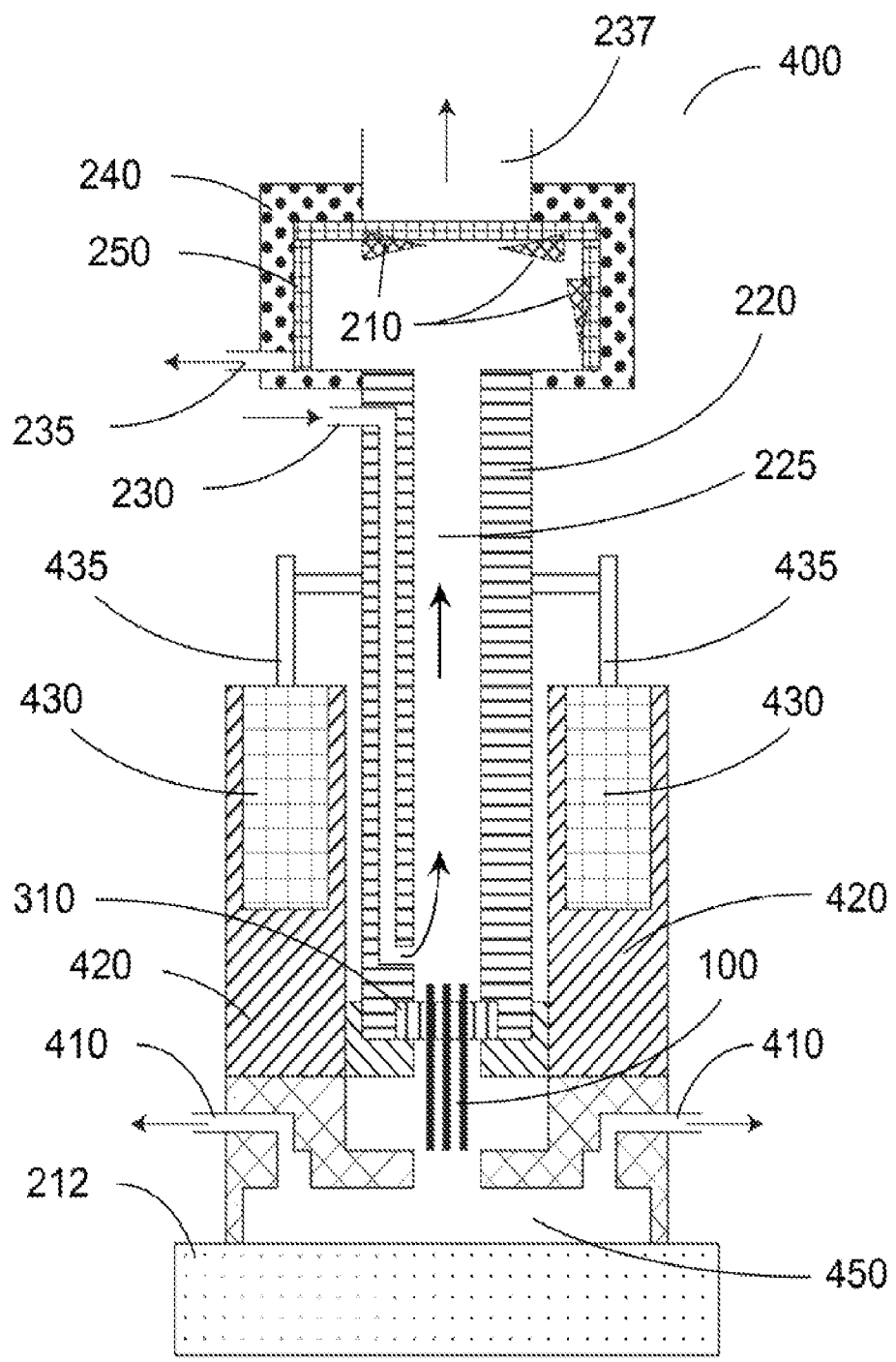
FIGS. 4A and 4B are cross-sectional views of diagrams of an exemplary apparatus for harvesting tissue samples in operation in accordance with still further exemplary embodiments of the present disclosure, performing further exemplary operations.
Figure 4B:
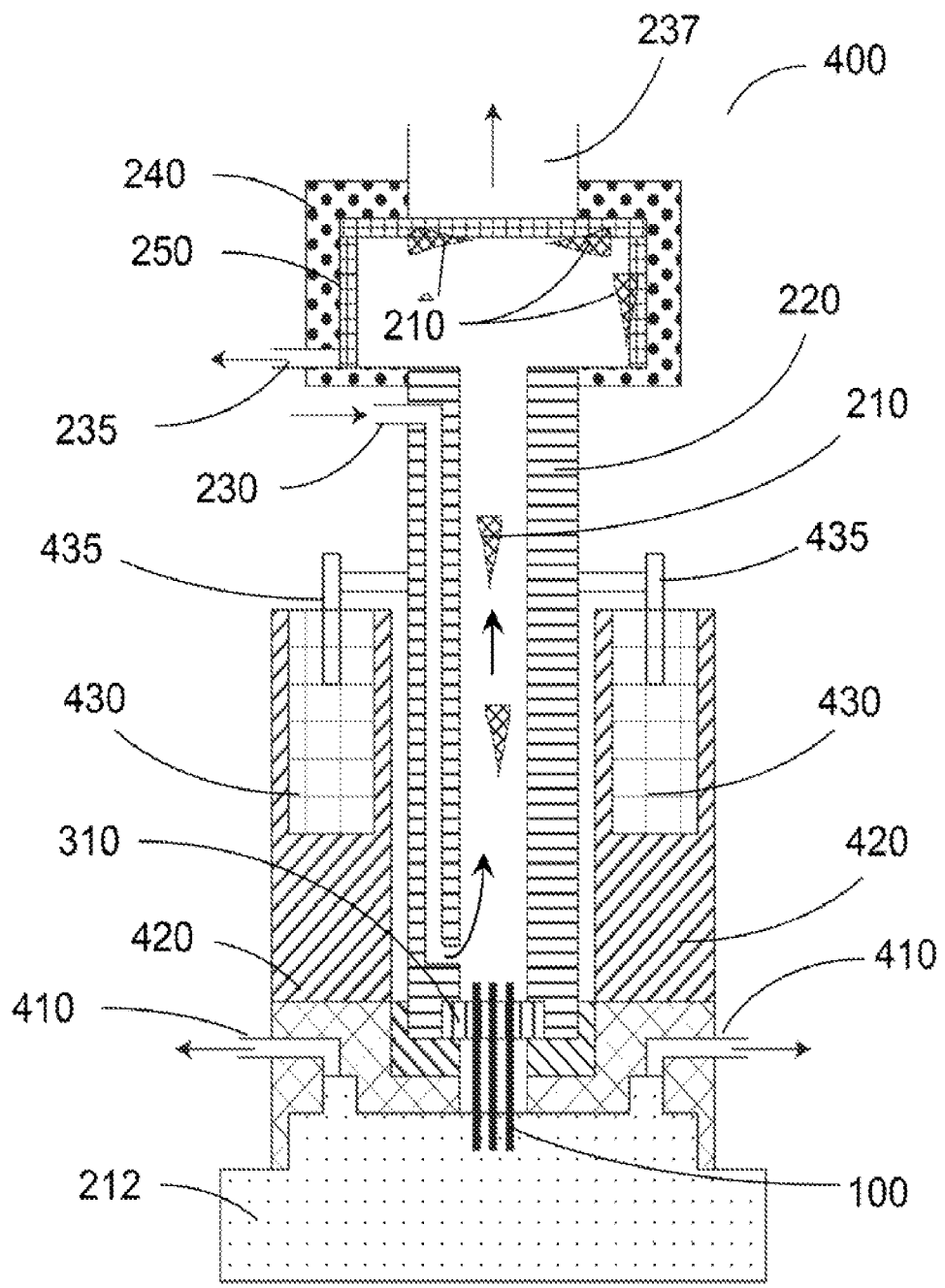

According to a further exemplary embodiment of the present disclosure, another exemplary apparatus can be provided, is shown in FIGS. 4A and 4B that can include the harvesting needle(s) 100 secured to the hub 310. The apparatus 400 shown in FIGS. 4A and 4B has many features similar to those shown and described for the apparatus 200, 300 and/or 350 shown in FIG. 2, FIG. 3A and FIG. 3B, respectively. These features include, e.g., the housing 220 with the fluid conduit 225, the harvesting needle(s) 100, the fluid inlet 230 and the outlet 235, the upper chamber 240, the optional vent 237, and the filter arrangement 250. One or more harvesting needles 100 can be attached or affixed to the hub 310.

The exemplary apparatus 400 can include a base 420 that can be slidably engaged with the housing 220, e.g., such that the housing 220 can move up and down over a particular distance relative to the base 420. One or more solenoid coils 430 can be coupled or affixed to the base 420, and a solenoid core 435 can be located at least partially within the solenoid coil 430 and mechanically coupled to the housing 220. With such exemplary configuration, the solenoid(s) 430 can be configured to move the housing 220 and the attached needles 100 up and down relative to the base 420, thereby inserting and withdrawing the needles 100 from the donor tissue 212. One or more O-rings or similar sealing arrangements can be provided to maintain a fluid-tight seal between the housing 200 and the hub 310, and also between the housing 220 and the base 420 when the housing 220 is translated during operation of the apparatus 400. A linear bearing can optionally be provided to maintain support and alignment of the housing 220 within the base 420 during operation of the apparatus 400.

For example, the apparatus 400 of FIG. 4A shows the solenoids 430 which are not activated. In this exemplary state, the harvesting needles 100 are retracted so that they are close to but not protruding from, a lower surface of the base 420. In operation, the base 420 can be placed on the surface of the donor site tissue 212 to be harvested, with the solenoids 430 off, as shown in FIG. 4A. A pump arrangement or the like (not shown) can be activated to supply fluid to the inlet 230 and circulate it through the conduit 225, as described herein.

The solenoids 430 can then be activated, such that the cores 435 are drawn downward, such that the housing 220 with mechanically coupled needles 110 are also pulled downward with respect to the base 420, as shown in FIG. 4B. This exemplary motion can result in the harvesting needles 100 protruding beyond a lower surface of the base 420, causing the needles 110 to pierce the tissue 212 of the donor site and separate MTCs 210 from the surrounding tissue 212, as described herein. The MTCs 210 can then be withdrawn from the needles 100 such that they flow through the conduit 225 with the fluid and can be deposited in the filter arrangement 250. The solenoids 430 can then be deactivated, such that the housing 220 rises relative to the base 420 (e.g., using springs or the like to return the housing to a raised position) and the needles 110 are withdrawn from the donor site 212 and back into the base 420, as shown in FIG. 4A. This exemplary procedure can be repeated at different locations on the donor site 212 to harvest additional MTCs 210. In an exemplary operation, such apparatus 400 can be used to harvest the MTCs 210 at a frequency between about 0.5 and about 2 Hz, e.g., with a time interval between successive penetrations of about 0.5 to 2 seconds. Certain exemplary modifications may be developed to allow faster harvesting rates, and slower rates can also be used if desired.

An adjusting arrangement such as, e.g., a screw-type adjuster or a spacer that can be an attached to the base 420, can be provided to control the maximum protrusion length of the needles 110 from a lower surface of the base 420 (thereby controlling a corresponding maximum penetration depth of the needles 100 into the donor site tissue 212).

In further exemplary embodiments of the present disclosure, other types of actuators can be used instead of or in addition to the solenoids 430. For example, one or more motors can be provided with a rotary/linear converter to convert rotary motion to a linear motion of the housing 220 relative to the base 420, e.g., at a controlled frequency and/or particular excursion distance. Other types of linear actuators can also be used to extend and withdraw the needles 100 from the tissue 212 beneath the apparatus 400.

The base 420 of the exemplary apparatus 400 can be structured to include a recess 450 that can form an enclosed volume between the tissue surface 212 and a lower surface of the base 420 adjacent to the needles 100, as shown in FIG. 4A. Such exemplary recess 450 can be formed, e.g., by providing the base 420 with a rim or edge that can rest on the donor site tissue 212 while a lower surface of the base 420 remains a small distance above the tissue surface. One or more vacuum ducts 410 can be provided in communication with the enclosed volume. Application of a low-pressure or vacuum source (not shown) to the vacuum duct(s) 410 can cause the surface of the donor site tissue 212 to be pulled up into the recess 450, as shown in FIG. 4B.

This exemplary deformation can stretch the surface and provide tension, which may provide several benefits. For example, stretching the tissue surface can mechanically stabilize it such that the needles 100 can penetrate the stretched tissue 212 more easily than they may penetrate unstretched, resilient tissue. Further, pulling the tissue surface upward using low pressure such that it contacts a lower surface of the base 420, as shown in FIG. 4B, can facilitate an accurate insertion depth of the needles 100. In certain embodiments, the needles 100 can be in a fixed position relative to the base 420 such that they remain protruding a small distance from the lower surface, as shown in FIG. 4B.

Instead of forcing the needles 100 into the tissue 212, as described herein, the tissue 212 can be pulled up onto the needles 100 such that they pierce the tissue 212, as shown in FIG. 4B. The low pressure can then be released to allow the tissue 212 to relax and fall off the needles 110, optionally assisted with a positive pressure being applied to the vacuum ducts 410. An exemplary application of low (and/or optionally high) pressure to the vacuum ducts 410 can be done, for example, using a conventional pump arrangement or other source(s) of low and high pressure, together with an appropriate valve arrangements to control the application and release of pressure differences in the ducts 410. The timing of such pressure cycles can be coordinated with the activation/deactivation of the solenoids 430. Such exemplary chamber 450 with the vacuum ducts 410 can also be used with any of the other exemplary embodiments described herein.

According to still further exemplary embodiments of the present disclosure, the surface of the donor site tissue 212 can be stretched or stabilized using other procedures, e.g., by manually stretching the surface with fingertips before inserting the needles 100. In yet further exemplary embodiments of the present disclosure, the donor site tissue 212 can be pre-cooled or partially frozen prior to insertion of the harvesting needles 100, e.g., using convective or conductive techniques such as a cryospray or contact with a cooled object. The exemplary cooling of the donor site tissue 212 can make it more rigid and facilitate insertion of the harvesting needles 100. In still further embodiments a mechanical surface clamp or spreader can be applied around the donor site region to stretch the tissue 212 before inserting the needles 100. Such procedures can be performed with any of the exemplary devices and methods described herein.

The exemplary apparatuses 200, 300, 350, 400 can be provided with various numbers of the harvesting needles 100. For example, in addition to a single one of the needles 100, arrays of 4, 6, 8, 9, 12 or more of the needles 100 can be used, and they can be affixed to a hub 310 to facilitate insertion and removal of the needles 100 from the exemplary apparatuses 200, 300, 350, 400 as a group. The needles 100 can be provided in various geometrical arrangements such as, e.g., a square or triangular pattern. Providing a hub with a larger number of needles can increase the efficiency and speed of harvesting MTCs 210, as more MTCs 210 (one per needle 100) can be harvested with each insertion-and-withdrawal cycle of the needles 100. However, a very large number of needles 100 can increase the force required to advance all of the needles 100 into the donor site tissue 212 simultaneously, and can increase the complexity of manufacturing the hub-needle component. According still additional exemplary embodiments of the present disclosure, the hub arrangements can have between about 4 and 25 needles coupled thereto.

The needles 100 can be spaced apart an appropriate distance to facilitate harvesting of a large number of the MTCs 210 from a donor site 212 while maintaining healthy tissue between the removed tissue samples 210 to promote rapid healing of the donor site 212, prevent formation of scars or markings, etc. For example, the spacing between adjacent needles 100 can be about 1-2 mm, or up to about 5 mm. Larger spacings can be used in certain embodiments, but this can require a correspondingly larger width of the overall apparatus to accommodate the larger hub. The MTCs 210 can be harvested over a larger area of tissue 212 by moving the exemplary apparatuses 200, 300, 350, 400 to different locations before each needle insertion procedure.

The exemplary embodiments described herein can include the fluid conduit 225 that is substantially vertical. In further exemplary embodiments of the present disclosure, other orientations of the conduit 225 can be provided. For example, the conduit can be substantially horizontal, with the inlet 230 and the outlet 235 can be provided at opposing ends of such a conduit 225, and the proximal ends of the needles 100 protruding into the conduit 225 such that the liquid flows past this end of the needles 100. Such an exemplary configuration can also provide a simpler, e.g. linear, conduit geometry that may be easier to manufacture and/or clean, may result in fewer pressure drops along the fluid path, etc. Other exemplary orientations of the conduit 225 or shapes thereof, such as a curved conduit, can also be provided in still further exemplary embodiments of the present disclosure.

According to still additional exemplary embodiments of the present disclosure, at least two of the needles 100 can be separately actuated, e.g., such that they pierce the tissue 212 at different times. For example, two or more actuators can be coupled to different ones of the needles. Alternatively, a singular actuator can be provided that is configured to advance different ones of the needles at different times. Such 'staggering' of penetrations can reduce the maximum force needed to advance the needles into the tissue.

Other needle cross-sectional shapes can be used with the various embodiments described herein to harvest the MTCs 210 having different geometric characteristics. Although circular cross-sections are most common, needles 100 having oval, square, or triangular cross-sections, or combinations thereof in multi-needle devices, can also be used.

In further embodiments of the present disclosure, the methods and apparatus described herein can be applied to other tissues besides skin tissue. Thus, the MTCs 210 can be harvested from a variety of organs or tissue structures, which can facilitate rapid healing of a donor site while providing microscopic graft tissue suitable for placement at recipient sites, on scaffolds, within biocompatible matrices, etc.

It will thus be appreciated that those skilled in the art will be able to devise numerous systems, arrangements and methods which, although not explicitly shown or described herein, embody the principles of the present disclosure and are thus within the spirit and scope of the present disclosure. In addition, all publications, patents, and patent applications referenced herein are incorporated herein by reference in their entireties.

What is claimed is:

1. An apparatus comprising:
   a hub;
   a housing including a recess;
   a plurality of harvesting needles coupled to the hub, each of the plurality of harvesting needles configured to penetrate a skin tissue a particular depth, wherein the hub is configured to fit in the recess of the housing and the hub is removably coupled to the housing to facilitate removal of the plurality of harvesting needles;
   a conduit configured to facilitate flow of a fluid therethrough, wherein each of the plurality of harvesting needles is in communication with the conduit;
   a filter arrangement provided at least partially in a path of the fluid; and
   a base attached to an end of the housing and configured to be placed on a surface of the skin tissue the base including an opening configured to form an enclosed volume above the surface of the skin tissue;
   wherein when the plurality of harvesting needles are in a retracted state, the plurality of harvesting needles do not protrude from a lower surface of the base; and
   wherein when the plurality of harvesting needles are pulled downward, the plurality of harvesting needles protrudes beyond the lower surface of the base.

2. The apparatus of claim 1, wherein the base is movably coupled to the housing along an axis, and
   wherein the housing is configured to insert and withdraw the plurality of harvesting needles from the skin tissue when the housing is translated back and forth along the axis relative to the base.

3. The apparatus of claim 1, wherein each of the plurality of harvesting needles has an inner diameter of less than 1 mm.

4. The apparatus of claim 1, further comprising:
   an actuator configured to move the plurality of harvesting needles into the skin tissue; and
   a spring configured to withdraw the plurality of harvesting needles out from the skin tissue.

5. The apparatus of claim 1,
   wherein in the retracted state, a distal end of each of the harvesting needles is positioned above the recess; and
   wherein when each of the harvesting needles is pulled downward, the distal end of each harvesting needle extends through the recess and pierces the skin tissue.

6. The apparatus of claim 1, wherein the conduit passes at least partially through the housing;
   wherein a distal portion of each of the plurality of harvesting needles is structured to be inserted, into the skin tissue to remove at least one portion of the skin tissue therefrom when each of the plurality of harvesting needles is withdrawn from the skin tissue; and wherein, in operation, the fluid flows through the conduit so as to remove the at least one portion of the skin tissue from each of the plurality of harvesting needles, and transport the at least one portion of the skin tissue to the filter arrangement.

7. The apparatus of claim 6, further comprising:
a chamber in fluid communication with the conduit, the filter arrangement positioned within the chamber to define a first side of the filter arrangement and a second side of the filter arrangement; and
a vent provided in fluid communication with the conduit, the vent positioned on the second side of the filter arrangement to facilitate entrained gas from passing from the first side of the filter arrangement, through the filter arrangement to the second side of the filter arrangement, and out the vent; and
wherein the filter arrangement blocks the at least one portion of the skin tissue from passing through the filter arrangement into the vent.

8. The apparatus of claim 1, further comprising a valve positioned between the plurality of harvesting needles and the filter arrangement;
wherein the valve is configured to open to facilitate movement of the fluid and a portion of the skin tissue harvested using at least one of plurality of harvesting needles through the valve; and
wherein the valve is configured to close when the plurality of harvesting needles are not positioned within the skin tissue to direct some fluid through the at least one of the plurality of harvesting needles to clean or unblock the at least one of the plurality of harvesting needles.

9. The apparatus of claim 1, further comprising a sensor configured to detect a presence of at least one portion of the skin tissue within the conduit.

10. An apparatus comprising:
a plurality of harvesting needles each of which is configured to penetrate skin tissue;
a housing including a recess;
a hub that is configured to fit in the recess of the housing, the plurality of harvesting needles coupled to the hub, the hub being removably coupled to the housing to facilitate removal of the plurality of harvesting needles;
a base configured to be placed on a surface of the skin tissue, wherein the base includes an opening configured to form an enclosed volume above the surface of the skin tissue, wherein in a retracted state, a distal end of each of the harvesting needles is positioned outside of the opening, and wherein when each of the harvesting needles is pulled downward, the distal end of each of the harvesting needles extends through the opening and pierces the skin tissue;
a conduit fluidly coupled to each of the plurality of harvesting needles, the conduit configured to facilitate flow of a fluid therethrough; and
a filter arrangement provided at least partially in a path of the fluid;
wherein a distal portion of each of the plurality of harvesting needles is configured to be inserted into the skin tissue to remove at least one portion of the skin tissue therefrom when the harvesting needle is withdrawn from the skin tissue; and
wherein, in operation, the fluid flows through the conduit so as to remove the at least one portion of the skin tissue from each of the plurality of harvesting needles, and transport the at least one portion of the skin tissue to the filter arrangement, which retains the at least one portion of the skin tissue.

11. The apparatus of claim 10, further comprising an actuator configured to move the plurality of harvesting needles into the skin tissue.

12. The apparatus of claim 10, wherein in the retracted state each of the harvesting needles does not protrude from a lower surface of the base; and
wherein when each of the harvesting needles is pulled downward, each of the harvesting needles protrudes beyond the lower surface of the base.

13. The apparatus of claim 10, further comprising a valve positioned between the plurality of harvesting needles and the filter arrangement; and
wherein the valve is configured to close when a first harvesting needle of the plurality of harvesting needles is not positioned within the skin tissue to direct some fluid through the first harvesting needle in a direction from a proximal end of the first harvesting needle to a distal end of the first harvesting needle to clean or unblock the first harvesting needle.

14. An apparatus comprising:
a harvesting needle configured to penetrate skin tissue;
a conduit fluidly coupled to the harvesting needle, the conduit configured to facilitate flow of a fluid therethrough;
a filter arrangement provided at least partially in a path of the fluid;
a first pressure sensor and a second pressure sensor, the first and second pressure sensors being configured to detect a pressure differential across the filter arrangement to ascertain whether the filter arrangement is clogged;
wherein a distal portion of the harvesting needle is configured to be inserted into the skin tissue to remove the portion of the skin tissue therefrom when the harvesting needle is withdrawn from the skin tissue; and
wherein, in operation, the fluid flows through the conduit so as to remove the portion of the skin tissue from the harvesting needle, and transport the portion of the skin tissue away from the harvesting needle and to the filter arrangement, which retains the portion of the skin tissue.

15. The apparatus of claim 14, further comprising a third sensor and a controller in communication with the third sensor, the third sensor being configured to provide a parameter to the controller;
wherein the controller is configured to control a flow rate or a composition of the fluid, based on the parameter; and
wherein the parameter is at least one of a flow rate of the fluid, or indicative of a composition of the fluid.

16. The apparatus of claim 14, further comprising:
a housing that is coupled to the harvesting needle;
a flexible tube coupled to the housing, the flexible tube fluidly coupled to the conduit; and
a receiving substrate positioned outside of the housing that includes the filter arrangement; and
wherein a position of an end of the flexible tube and the receiving substrate is adjustable to change the location in which the portion of the skin tissue is deposited on the filter arrangement.

* * * * *

UNITED STATES PATENT AND TRADEMARK OFFICE
CERTIFICATE OF CORRECTION

| | | |
|---|---|---|
| PATENT NO. | : 11,717,317 B2 | Page 1 of 1 |
| APPLICATION NO. | : 14/421592 | |
| DATED | : August 8, 2023 | |
| INVENTOR(S) | : Richard R. Anderson et al. | |

It is certified that error appears in the above-identified patent and that said Letters Patent is hereby corrected as shown below:

In the Specification

Column 2, Line 51, "pant" should be --part--.

Column 6, Line 60, "by it gentle" should be --by a gentle--.

Column 10, Line 49, "performed, using" should be --performed, e.g., using--.

Column 11, Line 65, "be an attached" should be --be attached--.

Signed and Sealed this
Seventeenth Day of October, 2023

Katherine Kelly Vidal
*Director of the United States Patent and Trademark Office*